(12) United States Patent  (10) Patent No.: US 8,225,664 B1
Sokol et al.  (45) Date of Patent: Jul. 24, 2012

(54) LAMB WAVES FOR LASER BOND INSPECTION

(75) Inventors: David W. Sokol, Dublin, OH (US);
Craig T. Walters, Powell, OH (US);
Kevin R. Housen, Tacoma, WA (US);
Richard H. Bossi, Renton, WA (US);
Steven M. Toller, Dublin, OH (US)

(73) Assignee: LSP Technologies, Dublin, OH (US)

( * ) Notice: Subject to any disclaimer, the term of this patent is extended or adjusted under 35 U.S.C. 154(b) by 700 days.

(21) Appl. No.: 11/873,571

(22) Filed: Oct. 17, 2007

(51) Int. Cl.
*G01N 29/04* (2006.01)

(52) U.S. Cl. .......................................... 73/588; 73/827

(58) Field of Classification Search ............... 73/150 A, 73/88, 642, 760, 800, 827, 588, 597; 156/344; 29/402.03, 403.3
See application file for complete search history.

(56) References Cited

U.S. PATENT DOCUMENTS

| | | | | |
|---|---|---|---|---|
| 4,155,627 A * | 5/1979 | Gale et al. | ..................... | 359/568 |
| 4,243,867 A * | 1/1981 | Earle et al. | ............... | 219/121.63 |
| 4,405,238 A * | 9/1983 | Grobman et al. | ............ | 356/401 |
| 5,561,613 A * | 10/1996 | Kobayashi et al. | ........... | 702/158 |
| 5,907,098 A * | 5/1999 | Tsuboi et al. | .................... | 73/579 |
| 5,996,415 A * | 12/1999 | Stanke et al. | .................... | 73/597 |
| 6,041,020 A * | 3/2000 | Caron et al. | .................. | 367/149 |
| 6,052,191 A * | 4/2000 | Brayden et al. | ............... | 356/630 |
| 6,066,830 A * | 5/2000 | Cline et al. | ............... | 219/121.69 |
| 6,069,693 A * | 5/2000 | Licchesi | ..................... | 356/237.1 |
| 6,158,285 A * | 12/2000 | Latimer et al. | ..................... | 73/643 |
| 6,234,025 B1 * | 5/2001 | Gieske et al. | .................... | 73/642 |
| 6,512,584 B1 * | 1/2003 | O'Loughlin et al. | ......... | 356/388 |
| 6,554,921 B2 * | 4/2003 | Sokol et al. | ..................... | 148/508 |
| 6,848,321 B2 * | 2/2005 | Bossi et al. | ...................... | 73/842 |
| 7,287,902 B2 * | 10/2007 | Safai et al. | ......................... | 374/5 |
| 7,507,312 B2 * | 3/2009 | Bossi et al. | ..................... | 156/714 |
| 7,507,321 B2 * | 3/2009 | Aksu et al. | ..................... | 205/261 |
| 7,509,876 B1 * | 3/2009 | Sokol et al. | ..................... | 73/827 |
| 7,574,916 B2 * | 8/2009 | Tillotson | ......................... | 73/588 |
| 7,765,861 B2 * | 8/2010 | Jacquemin | ................. | 73/150 A |
| 7,770,454 B2 * | 8/2010 | Sokol et al. | ..................... | 73/588 |
| 7,775,122 B1 * | 8/2010 | Toller et al. | ..................... | 73/827 |
| 7,798,000 B1 * | 9/2010 | Murray et al. | ................... | 73/597 |
| 2005/0120803 A1 * | 6/2005 | Sokol et al. | ..................... | 73/801 |

OTHER PUBLICATIONS

Sokol et al., Laser System and Method for Non-Destructive Bond Detection and Evaluation, U.S. Appl. No. 10/950,865, filed Sep. 27, 2004.
Walters, Craig T., Apparatus and Method for Non-Destructive Testing, U.S. Appl. No. 11/227,745, filed Sep. 15, 2005.
Toller et al., Laser Bond Inspection Using Annular Laser Beam, U.S. Appl. No. 11/873,677, filed Oct. 17, 2007.
Toller et al., Tape Overlay for Laser Bond Inspection, U.S. Appl. No. 11/873,705, filed Oct. 17, 2007.

* cited by examiner

*Primary Examiner* — Sang Nguyen
(74) *Attorney, Agent, or Firm* — Benjamein E. Kern (57) ABSTRACT

Exemplary embodiments are disclosed for the use of Lamb waves in laser bond inspection.

25 Claims, 10 Drawing Sheets

LAMB WAVES FOR LASER BOND INSPECTION

BACKGROUND

A need exists in industry for non-destructive inspection of composite structures assembled with adhesive bonds. Among other techniques, laser bond inspection (LBI) has proven useful. Normally, LBI involves deposition of laser energy onto the front surface of a first plate in a bonded article, generating compression waves that reflect off of the back surface of the bonded article as tensile waves, the tensile waves predominantly providing the stresses that interrogate the bond. The compression waves are generally longitudinal, having been driven normal to the plane of the first plate.

In a number of tasks, the use of longitudinal stress waves as generated in conventional LBI is impractical. For example, in circumstances where the first plate has a materially different acoustic impedance than the plate(s) or structure to which the first plate is bonded, the results (i.e., bond breaking and detection of bond breaking) can be inconsistent. Another exemplary circumstance may be where the bond to be tested is a face-sheet-to-core bond, wherein no back free surface is accessible to generate a tensile wave.

SUMMARY

In one embodiment, a method for laser bond inspection is provided, the method comprising: placing a laser source near a bonded article, the bonded article comprising a first plate and a structure to which the first plate is bonded, and wherein the laser source is configured to deposit a patterned laser beam onto the first plate such that Lamb waves propagate through the first plate; activating the laser source; and detecting surface motions.

In another embodiment, a method for interrogating a bond in a bonded article is provided, the bonded article being comprised of a first plate adhered to a second plate at the bond, the first plate and the second plate having different acoustic impedances, the method comprising: positioning a laser source near a surface of the first plate, wherein the laser source is configured to deposit a laser beam having a spatially varied irradiance pattern over the surface; activating the laser source, thereby propagating Lamb waves through the first plate; and detecting surface motions in the bonded article.

In still another embodiment, a method is provided for interrogating a bond in a bonded article, the bonded article being comprised of a face plate adhered to a core structure, comprising: positioning a laser source near a surface of the face plate, wherein the laser source is configured to deposit a laser beam having a spatially varied irradiance pattern onto the surface; activating the laser source, thereby propagating guided plate waves through the face plate to stress the bond; and detecting surface motions.

BRIEF DESCRIPTION OF THE DRAWINGS

The accompanying figures, which are incorporated in and constitute a part of the specification, illustrate various example systems, methods, results, and so on, and are used merely to illustrate various example embodiments. It should be noted that various components depicted in the figures may not be drawn to scale. The exemplary results presented in the figures are presented for purposes of illustration only, and should not be considered in any way as limiting.

DETAILED DESCRIPTION

The present embodiments disclose the use of Lamb waves for use in laser bond inspection. The present embodiments will find use in any field in which non-destructive bond inspection is required or desired. The present embodiments will also find use when the use of longitudinal stress wave propagation in laser bond inspection is undesirable or impractical.

Lamb waves are guided waves that propagate in thin plates. Lamb waves can have very low attenuation in the absence of energy absorbing mechanisms such as bond failure. The lowest order symmetric mode is a thickness bulging and contracting. The lowest order asymmetric mode is a flexing of the plate. These modes can be sensed and differentiated by surface motion detectors, such as, for example, an electromagnetic acoustic transducer (EMAT) or a velocity interferometer for surfaces of any reflectance (VISAR), placed on both sides of the plate at a sufficient distance from the source of generation. Excitation of Lamb waves can be accomplished by forcing spatially varying surface deflection of the correct wavelength.

Figure 1:
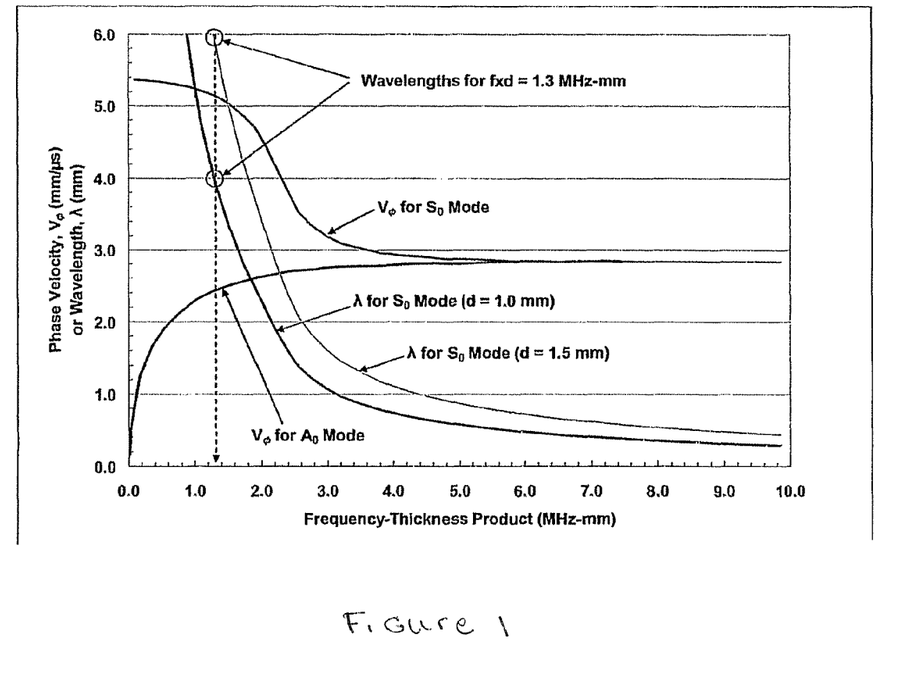
FIG. 1 illustrates exemplary dispersion relationships for the lowest order Lamb waves in aluminum plates of varying thicknesses.

FIG. 1 presents the dispersion relationships for the lowest order Lamb waves in aluminum plates of varying thicknesses. The zero-order symmetric mode, $S_0$, has the lowest attenuation and is simply a bulging and contracting motion that moves along within the plate. The asymmetric mode, $A_0$, is a snake-like bulk movement within the plate.

In one embodiment, a method for laser bond inspection is provided, the method comprising: placing a laser source near a bonded article, the bonded article comprising a first plate and a structure to which the first plate is bonded, and wherein the laser source is configured to deposit a patterned laser beam onto the first plate such that Lamb waves propagate through the first plate; activating the laser source; and detecting surface motions. Of course, one of ordinary skill in the art will readily recognize that the proximity and/or orientation of the laser source relative to the bonded article may vary, and may be any operable or workable range and/or displacement.

In some instances, the method may involve set-ups similar to that involved in laser shock processing. Laser shock processing assemblies and methods are described in U.S. Pat. Nos. 5,741,559, 5,911,891, 6,412,331, 5,131,957, and U.S. patent application Ser. No. 10/950,865, each of which is incorporated by reference herein in its entirety.

In one embodiment of the method, the structure may be a second plate having a different acoustic impedance than the first plate. Alternatively, the structure may be a multilayered laminate wherein one or more of the layers is a plate having a different acoustic impedance than the first plate. In still another alternative, the first plate may be a face plate and the structure may be a core of the bonded article.

In one embodiment, the method may further comprise placing a striped mask between the laser source and the first plate. The method may further comprise imposing a square wave displacement pattern on a surface of the first plate.

In one embodiment of the method, the detecting may comprise detecting with an electromagnetic acoustic transducer (EMAT). The detecting may also comprise detecting with two electromagnetic acoustic transducers, one positioned proximate to each of opposite sides of the bonded article. In another embodiment, the detecting may comprise detecting with a velocity interferometer for surfaces of any reflectance (VISAR). The detecting may also comprise detecting with two velocity interferometers for surfaces of any reflectance, one positioned proximate to each of opposite sides of the bonded article.

In one embodiment, the method further comprises applying a substantially opaque overlay to a surface of the first plate and providing a substantially transparent overlay over the opaque overlay. In one embodiment, the substantially opaque overlay may comprise black tape or black paint. The substantially transparent overlay may comprise flowing water. In an alternative embodiment, the substantially opaque overlay and the substantially transparent overlay are collectively part of a tape overlay, the tape overlay comprising a substantially opaque overlay comprising aluminum backed tape; a substantially transparent overlay comprising clear tape; and a retro-reflective layer adhered to the transparent overlay and being positioned substantially over the center of the tape overlay; wherein the retro-reflective layer is configured to indicate surface motions in the bonded article when placed in operable communication with the surface motion detector.

In one embodiment, a method is provided for interrogating a bond in a bonded article, the bonded article being comprised of a first plate adhered to a second plate at the bond, the first plate and the second plate having different acoustic impedances, the method comprising: positioning a laser source near a surface of the first plate, wherein the laser source is configured to deposit a laser beam having a spatially varied irradiance pattern onto the surface; activating the laser source, thereby propagating Lamb waves through the first plate; and detecting surface motions.

In another embodiment of the method, the method may further comprise placing a striped mask between the laser source and the first plate. The method may also comprise producing a striped irradiance pattern over the surface. The method may additionally comprise imposing a square wave displacement pattern on a surface of the first plate. The method may further comprise selecting a wavelength of the laser beam such that the product of the frequency of the laser beam multiplied by the thickness of the first plate is less than 2 MHz·mm.

In one embodiment of the method, the detecting comprises detecting with an electromagnetic acoustic transducer. The detecting may also comprise detecting with two electromagnetic acoustic transducers, one positioned proximate to each of opposite sides of the bonded article. In one embodiment, the detecting comprises detecting with a velocity interferometer for surfaces of any reflectance. The detecting may also comprise detecting with two velocity interferometers for surfaces of any reflectance, one positioned proximate to each of opposite sides of the bonded article.

In one embodiment of the method, a substantially opaque overlay may be applied over the surface. A substantially transparent overlay may be provided over the opaque overlay.

In still another embodiment, a method is provided for interrogating a bond in a bonded article, the bonded article being comprised of a face plate adhered to a core structure, comprising: positioning a laser source near a surface of the face plate, wherein the laser source is configured to deposit a laser beam having a spatially varied irradiance pattern onto the surface; activating the laser source, thereby propagating guided plate waves through the face plate to stress the bond; and detecting surface motions.

In one embodiment of the method, a striped mask may be placed between the laser source and the face plate. The method may further comprise producing a striped irradiance pattern over the surface. The method may also comprise imposing a square wave displacement pattern on a surface of the face plate. In one embodiment, the method may comprise selecting a wavelength of the laser beam such that the product of the frequency of the laser beam multiplied by the thickness of the face plate is less than 2 MHz·mm.

In one embodiment of the method, the detecting comprises detecting with an electromagnetic acoustic transducer. The detecting may alternatively comprise detecting with two electromagnetic acoustic transducers, one positioned proximate to each of opposite sides of the bonded article. In an alternative embodiment, the detecting comprises detecting with a velocity interferometer for surfaces of any reflectance. The method may further comprise detecting surface motions with two velocity interferometers for surfaces of any reflectance, one positioned proximate to each of opposite sides of the bonded article.

The method may further comprise applying a substantially opaque overlay over the surface and providing a substantially transparent overlay over the opaque overlay.

Figure 2:
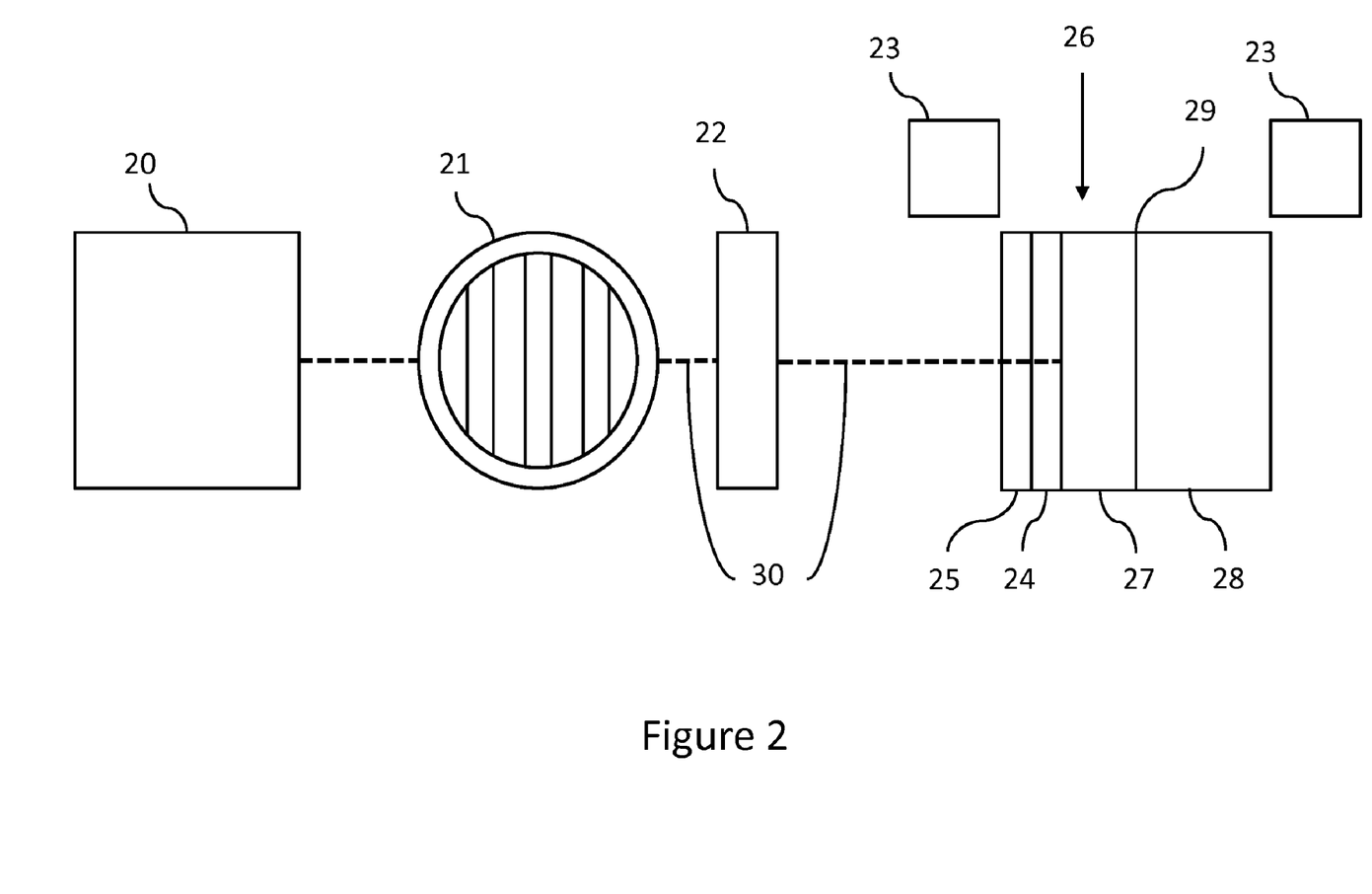
FIG. 2 illustrates an exemplary system for using Lamb waves to interrogate a bond.

FIG. 2 illustrates an exemplary system for using Lamb waves to interrogate a bond. With reference to FIG. 2, a laser source 20 is positioned near a bonded article 26. Bonded article 26 comprises a first plate 27 adhered to a structure 28 through bond 29. An LBI overlay may also be used. That is, the system may include a substantially opaque overlay 24 and a substantially transparent overlay 25. A mask 21 is placed between laser source 20 and a focusing lens 22. Laser source 20 is thus configured to deposit a patterned laser beam 30 onto first plate 27 such that Lamb waves propagate through first plate 27. Surface motions may be detected by surface motion detector(s) 23, which may be, for example, one or more EMAT gauges or VISAR probes. Patterned laser beam 30 may be in the form of a square wave displacement pattern.

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

The following examples are provided to illustrate various embodiments and shall not be considered as limiting in scope.

EXAMPLES

Lamb waves with high intensity laser pulses were generated using a striped irradiance pattern. A standard LBI overlay structure was used—that is, the substantially opaque overlay was black paint and the substantially transparent overlay was flowing water. A striped mask was also used. The stripe pattern was designed to impose a square wave displacement pattern on the front surface of the plate, with the displacement being created by the laser-generated stress waves in the stripe regions. The wavelength of the stripe pattern was selected to keep the frequency-plate thickness product (f×d) less than about 2 MHz·mm to minimize excitation of higher order modes. The light and dark traces in FIG. 1 present the calculated wavelengths for the $S_0$ mode for a 1.5 mm and a 1.0 mm thick plate, respectively. Stripe wavelengths of 6 mm and 4 mm were selected for convenience, which gave f×d=1.3 MHz·mm.

Figure 3:
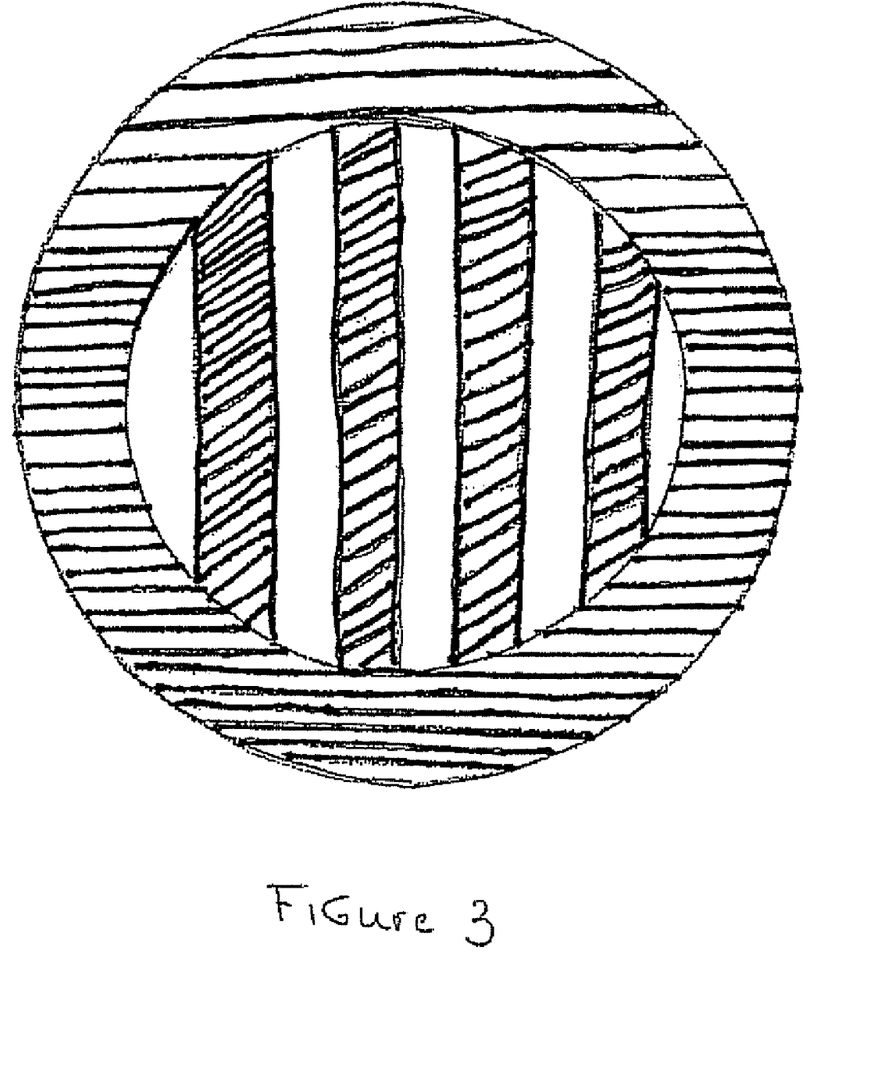
FIG. 3 illustrates an exemplary embodiment of an optical mask configured to generate a four-stripe irradiance pattern.

Masks were prepared to form the stripe pattern in the laser beam prior to focusing to the plate surface. An exemplary embodiment of a mask is shown in FIG. 3. As depicted, FIG. 3 illustrates an aluminum foil mask for a four-stripe pattern. When placed in front of the focusing lens of the laser source, four cycles of a square wave irradiance pattern are imposed on a 1.0 mm thick aluminum plate with a wavelength of 4 mm at the work surface. The beam diameter at the surface was 16 mm. Only one side of the plate was exposed.

When the stripes of the mask were placed in a vertical orientation, the Lamb waves propagated in a horizontal direction. An EMAT gauge was mounted on a translational stage so that it could be moved in a horizontal plane to fixed lateral positions relative to the beam axis. Identical EMAT gauges were located within 0.01 inch of opposite sides of the article and measured surface velocity perpendicular to the plate surface.

Figure 4:
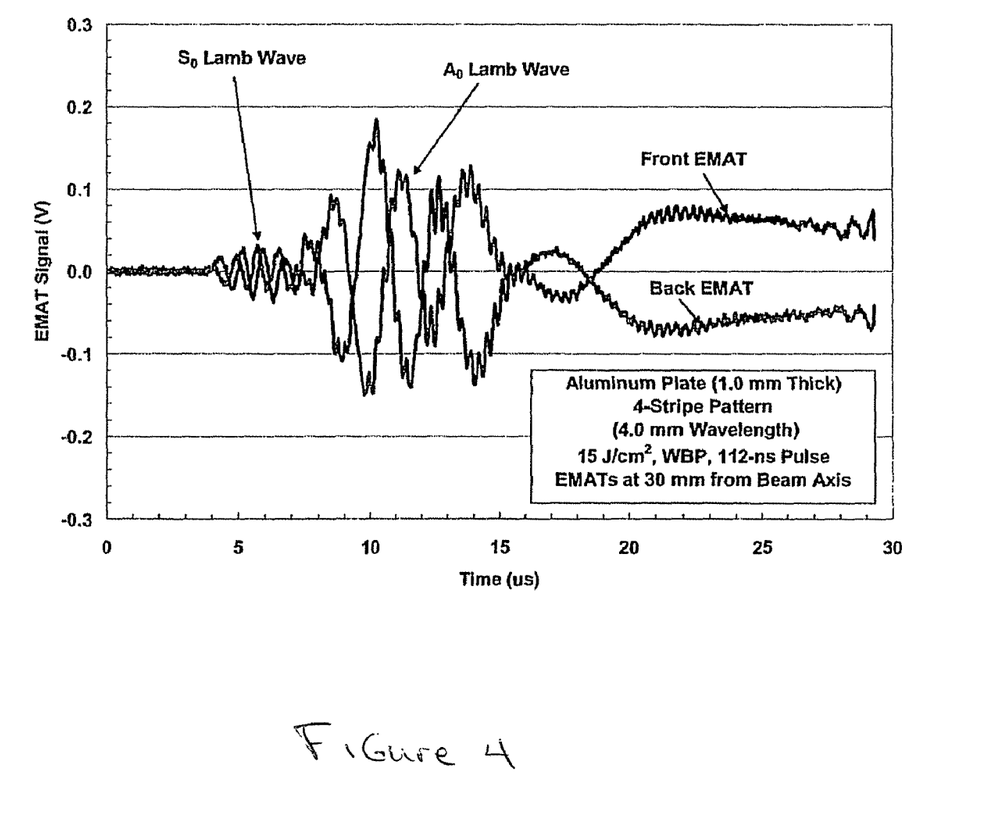
FIG. 4 illustrates exemplary experimental EMAT records for Lamb waves generated in a 1.0 mm thick aluminum plate.

Raw surface motion data for a typical test with the EMAT gauges located 30 mm from the beam axis are shown in FIG. 4. The light and dark traces shown in FIG. 4 show the front and back surface EMAT signals, respectively. A positive value corresponds to surface motion toward the gauge. Two wave packets are clearly seen in addition to some late-time plate motion and low amplitude high-frequency vibration. The first wave packet is the symmetric $S_0$ mode Lamb wave with an average arrival time of about 6 μs. The computed group velocity for the packet is, therefore, about 5 mm/μs, which is in agreement with theory. The two signals are phase shifted slightly, but, in general, show simultaneous motion of the surfaces toward each gauge (bulging). The second wave packet shows the opposite behavior which is characteristic of the snake-like motion of the anti-symmetric $A_0$ mode Lamb wave. The average arrival time of this wave packet is about 11 μs, which corresponds to a group velocity of about 2.7 mm/μs. This value is below the predicted value of 3.1 mm/μs, but is within experimental error. The magnitude of the asymmetric mode wave is much greater than that of the symmetric mode. This is likely due to the asymmetric excitation inherent with one-sided application of the stress wave. Simultaneous exposure of both sides of the plate would excite the symmetric mode preferentially.

Figure 5:
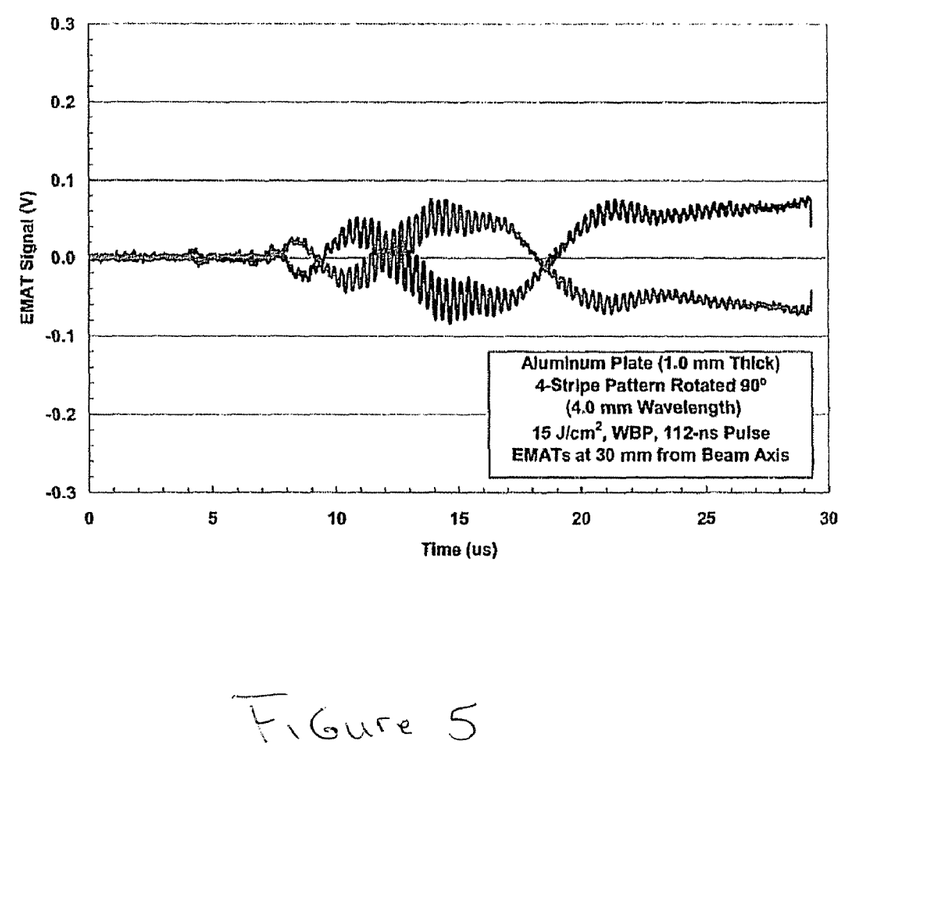
FIG. 5 illustrates exemplary experimental EMAT records generated in a 1.0 mm thick aluminum plate, wherein the optical mask was rotated to propagate Lamb waves 90 degrees to the EMAT locations.

To confirm that the observed wave packets were Lamb waves, the test was repeated with the mask rotated 90 degrees. Such a rotation causes propagation of the Lamb waves vertically, which is undetectable by the EMAT gauges. FIG. 5 illustrates the EMAT records and, in this case, no Lamb waves were observed. The low-frequency plate motion (asymmetric) and high frequency vibration (symmetric) were still present.

Figure 6:
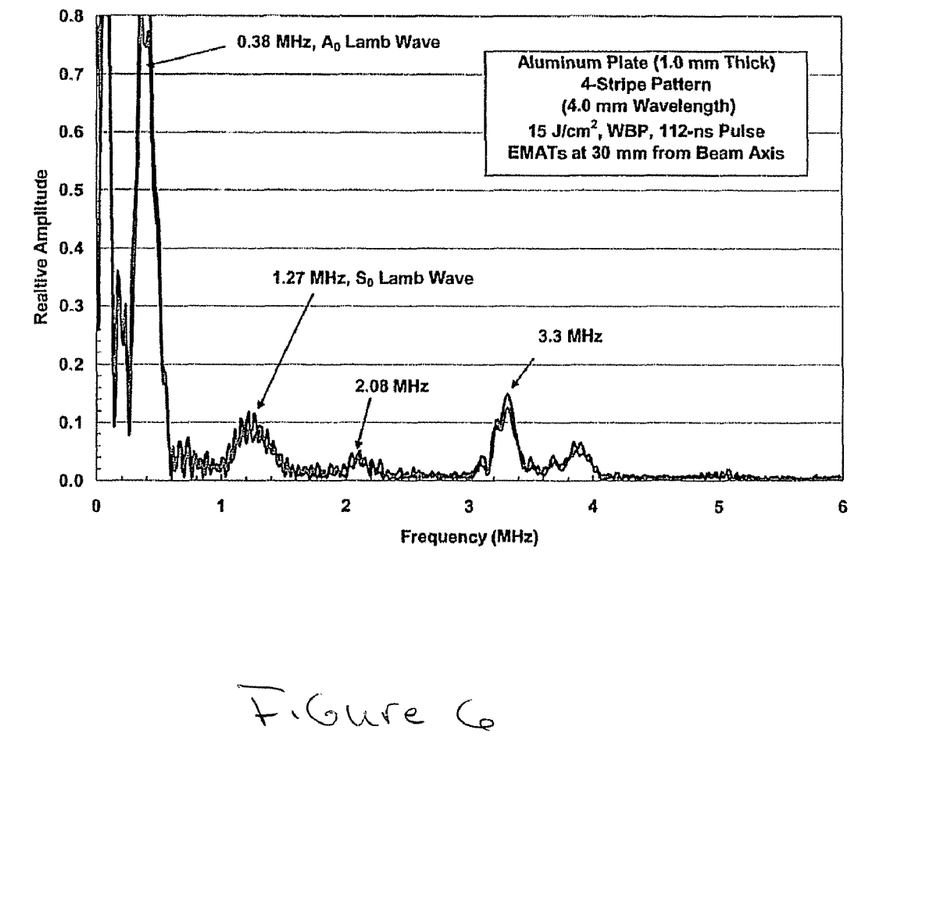
FIG. 6 illustrates an exemplary experimental frequency spectrum of EMAT records for Lamb waves generated in a 1.0 mm thick aluminum plate.
Figure 7:
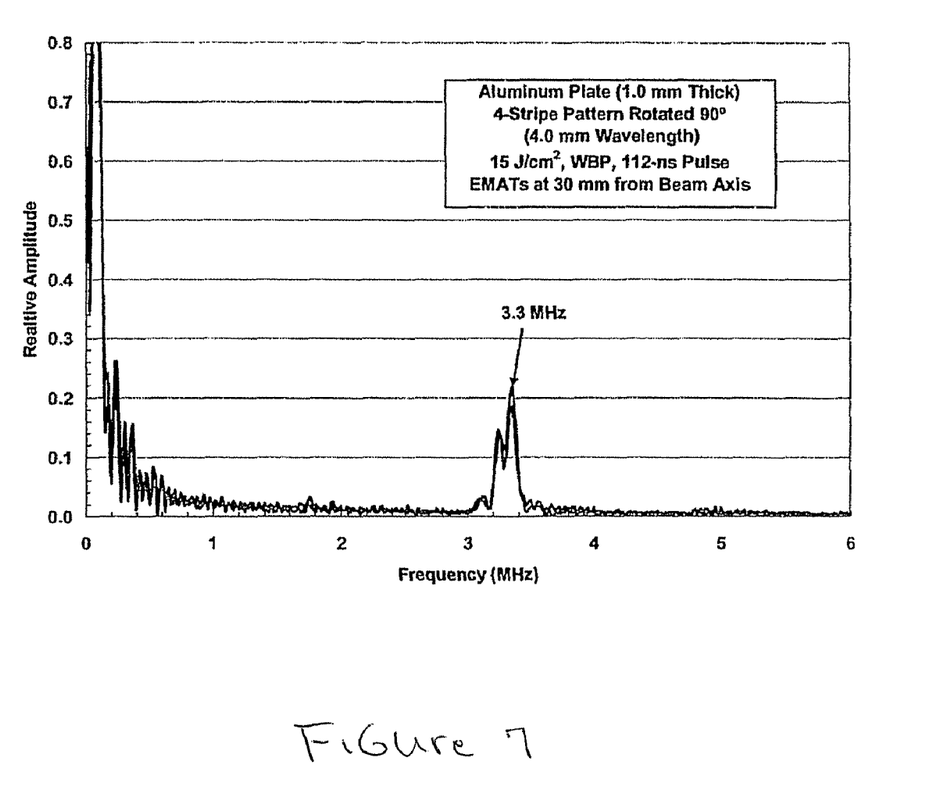
FIG. 7 illustrates an exemplary experimental frequency spectrum of EMAT records for Lamb waves generated in a 1.0 mm thick aluminum plate with the mask rotated to propagate Lamb waves 90 degrees to the EMAT locations.

The frequency spectra of the waves generated for the two cases presented above were calculated using a fast-Fourier transform algorithm. These results are presented in FIGS. 6 and 7. FIG. 6 illustrates an exemplary experimental frequency spectrum of EMAT records for Lamb waves generated in a 1.0 mm thick aluminum plate. FIG. 7 illustrates an exemplary experimental frequency spectrum of EMAT records for Lamb waves generated in a 1.0 mm thick aluminum plate with the mask rotated to propagate Lamb waves 90 degrees to the EMAT locations.

The feature centered near 1.27 MHz in FIG. 6 corresponds to the $S_0$ Lamb wave. This value is close to the value of 1.3 MHz predicted for the 4 mm wavelength stripe pattern as shown in FIG. 1 for the $S_0$ mode. The asymmetric $A_0$ mode has a lower phase velocity and, therefore, a lower frequency for the 4 mm wavelength excitation. The predicted frequency is 0.4 MHz, which is in good agreement with the feature seen in FIG. 6. The absence of Lamb wave frequencies in FIG. 7 confirms the measurement.

Figure 8:
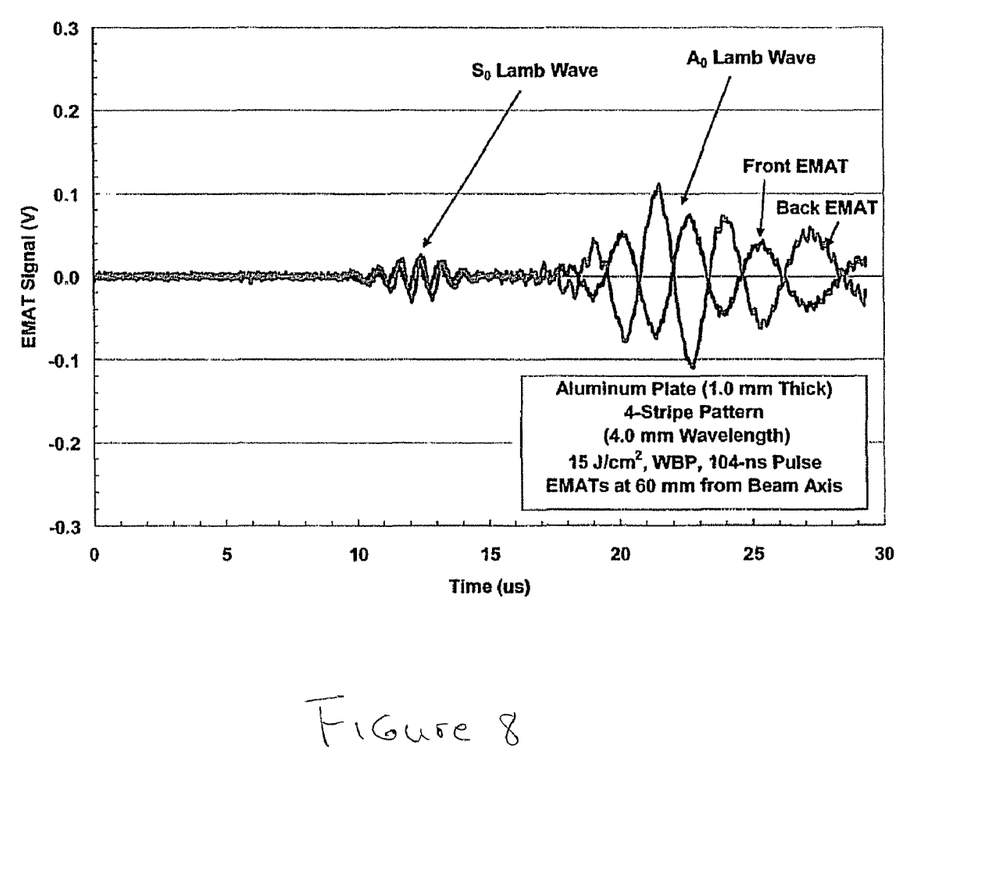
FIG. 8 illustrates exemplary experimental EMAT records for Lamb waves generated in a 1.0 mm thick aluminum plate at 60 mm from the beam axis.

FIG. 8 illustrates exemplary experimental EMAT records for Lamb waves generated in a 1.0 mm thick aluminum plate at 60 mm from the beam axis. In this case, the wave packets are more clearly separated because of the difference in group velocity. The calculated group velocities and frequencies were consistent with those determined for the 30 mm distance case.

Figure 9:
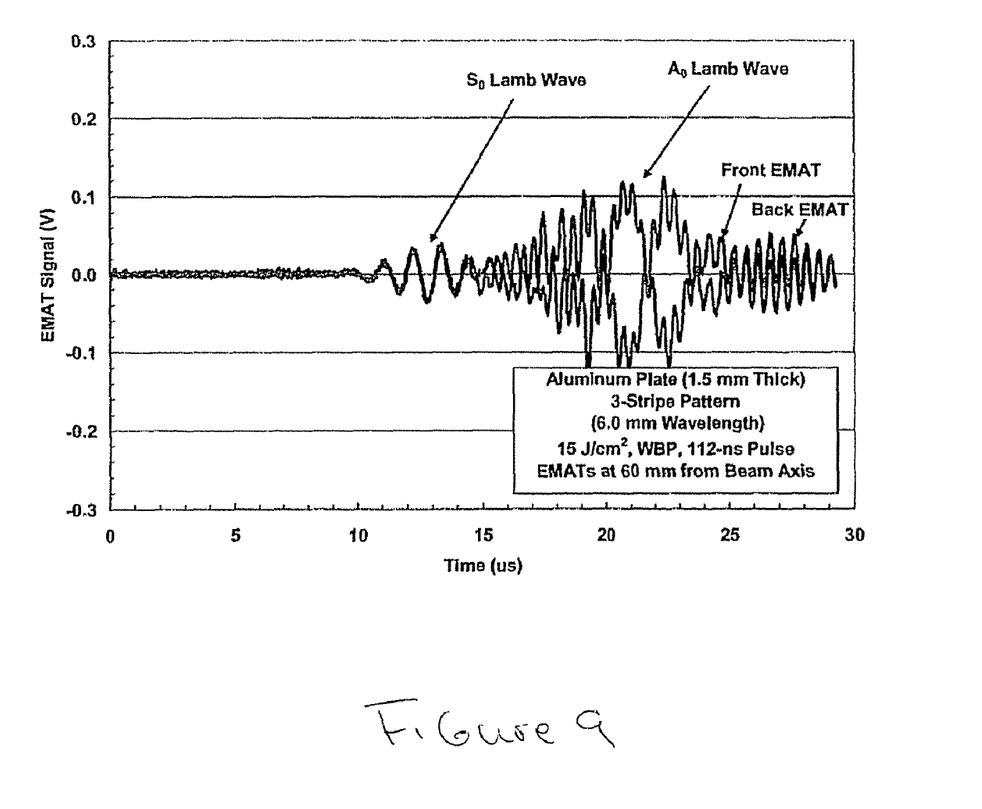
FIG. 9 illustrates exemplary experimental EMAT records for Lamb waves generated in a 1.5 mm thick aluminum plate at 60 mm from the beam axis.

Similar tests were performed for the 1.5 mm thick aluminum plate. FIG. 9 illustrates exemplary experimental EMAT records for Lamb waves generated in a 1.5 mm thick aluminum plate at 60 mm from the beam axis. The results are similar to those seen in FIG. 8, except for the superposition of a high frequency symmetric plate vibration not related to the Lamb wave.

Figure 10:
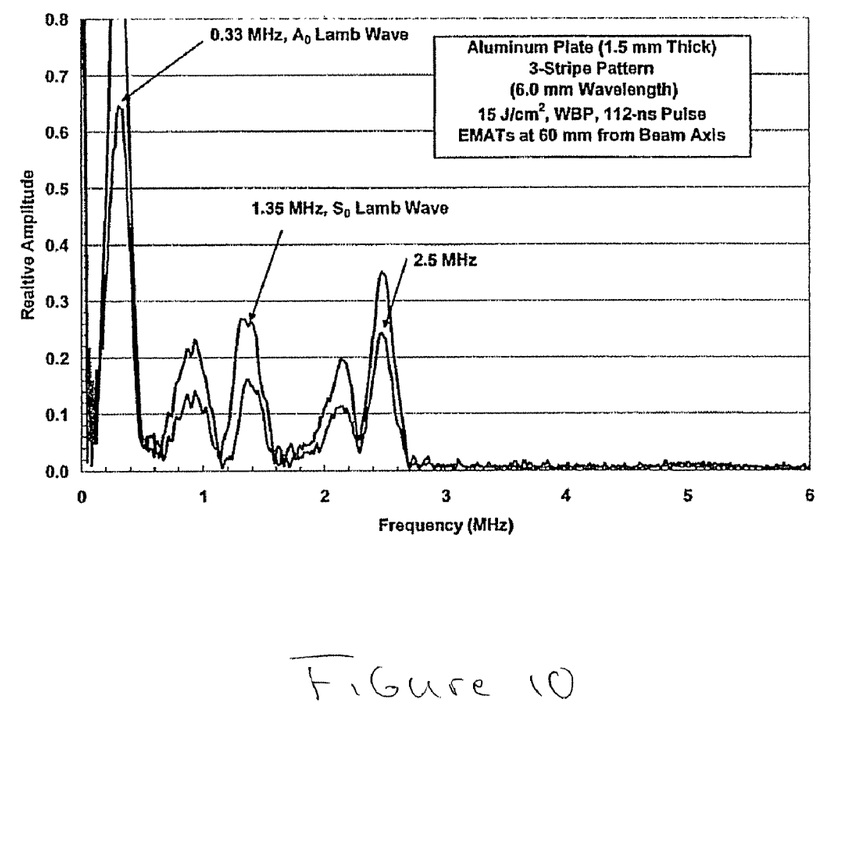
FIG. 10 illustrates an exemplary experimental frequency spectrum of EMAT records for Lamb waves generated in a 1.5 mm thick aluminum plate at 60 mm from the beam axis.

FIG. 10 illustrates an exemplary experimental frequency spectrum of EMAT records for Lamb waves generated in a 1.5 mm thick aluminum plate at 60 mm from the beam axis. In addition to the Lamb wave frequencies and the high-frequency plate vibration at 2.5 MHz, there are additional features near 0.9 MHz and 2.1 MHz. FIG. 10 was generated using a three-stripe pattern. The additional features correspond to additional modes generated by the three-stripe pattern. More cycles in the pattern would likely concentrate more energy in the intended Lamb wave modes.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" or "having" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A method for laser bond inspection, comprising:
    placing a laser source near a bonded article, the bonded article comprising a first plate and a structure to which the first plate is bonded, and wherein the laser source is configured to deposit a patterned laser beam onto the first plate such that Lamb waves propagate through the first plate;
    activating the laser source; and
    detecting surface motions, wherein the detecting comprises detecting with one or more surface motion detectors.

2. The method of claim 1, wherein the structure is a second plate having a different acoustic impedance than the first plate.

3. The method of claim 1, wherein the structure is a multilayered laminate wherein one or more of the layers is a plate having a different acoustic impedance than the first plate.

4. The method of claim 1, wherein the first plate is a face plate and the structure is a core of the bonded article.

5. The method of claim 1, wherein the one or more surface motion detectors comprises an electromagnetic acoustic transducer and/or a velocity interferometer for surfaces of any reflectance.

6. The method of claim 1, wherein the one or more surface motion detectors comprises two electromagnetic acoustic transducers, one positioned proximate to each of opposite sides of the bonded article.

7. The method of claim 1, wherein the one or more surface motion detectors comprises two velocity interferometers for surfaces of any reflectance, one positioned proximate to each of opposite sides of the bonded article.

8. The method of claim 1, further comprising placing a striped mask between the laser source and the first plate.

9. The method of claim 1, further comprising imposing a square wave displacement pattern onto the surface.

10. The method of claim 1, further comprising applying a substantially opaque overlay over the surface and providing a substantially transparent overlay over the opaque overlay.

11. The method of claim 10, wherein the applying a substantially opaque overlay comprises applying black paint or black tape.

12. The method of claim 11, wherein the providing a substantially transparent overlay over the opaque overlay comprises providing flowing water.

13. The method of claim 10, wherein the substantially opaque overlay and the substantially transparent overlay are collectively part of a tape overlay, the tape overlay comprising a substantially opaque overlay comprising aluminum backed tape; a substantially transparent overlay comprising clear tape; and a retro-reflective layer adhered to the transparent overlay and being positioned substantially over the center of the tape overlay; wherein the retro-reflective layer is configured to indicate surface motions in the bonded article when placed in operable communication with a surface motion detector.

14. A method for interrogating a bond in a bonded article, the bonded article being comprised of a face plate adhered to a core structure, comprising:
    positioning a laser source near a surface of the face plate, wherein the laser source is configured to deposit a laser beam having a spatially varied irradiance pattern onto the surface;
    activating the laser source, thereby propagating guided plate waves through the face plate to stress the bond; and
    detecting surface motions, wherein the detecting comprises detecting with one or more of an electromagnetic acoustic transducer and a velocity interferometer for surfaces of any reflectance.

15. The method of claim 14, further comprising imposing a square wave displacement pattern over the surface.

16. The method of claim 14, further comprising applying a substantially opaque overlay over the surface and providing a substantially transparent overlay over the opaque overlay.

17. The method of claim 14, further comprising selecting a wavelength of the laser beam such that the product of the frequency of the laser beam multiplied by a thickness of the face plate is less than 2 MHz·mm.

18. A method for laser bond inspection, comprising:
    placing a laser source near a bonded article, the bonded article comprising a first plate and a structure to which the first plate is bonded, and wherein the laser source is configured to deposit a patterned laser beam onto the first plate such that Lamb waves propagate through the first plate;
    activating the laser source; and
    detecting surface motions, wherein the detecting comprises detecting with one or more of an electromagnetic acoustic transducer and a velocity interferometer for surfaces of any reflectance.

19. The method of claim 18, wherein the structure is a second plate having a different acoustic impedance than the first plate.

20. The method of claim 18, wherein the structure is a multilayered laminate wherein one or more of the layers is a plate having a different acoustic impedance than the first plate.

21. The method of claim 18, wherein the first plate is a face plate and the structure is a core of the bonded article.

22. The method of claim 18, further comprising placing a striped mask between the laser source and the first plate.

23. The method of claim 18, further comprising imposing a square wave displacement pattern onto the surface.

24. The method of claim 18, further comprising applying a substantially opaque overlay over the surface and providing a substantially transparent overlay over the opaque overlay.

25. The method of claim 24, wherein the substantially opaque overlay and the substantially transparent overlay are collectively part of a tape overlay, the tape overlay comprising a substantially opaque overlay comprising aluminum backed tape; a substantially transparent overlay comprising clear tape; and a retro-reflective layer adhered to the transparent overlay and being positioned substantially over the center of the tape overlay; wherein the retro-reflective layer is configured to indicate surface motions in the bonded article when placed in operable communication with a surface motion detector.

* * * * *